United States Patent
Kobayashi et al.

(10) Patent No.: US 9,548,439 B2
(45) Date of Patent: Jan. 17, 2017

(54) POROSITY CONTROL IN PIEZOELECTRIC FILMS

(75) Inventors: Makiko Kobayashi, Montreal (CA); Cheng-Kuei Jen, Brossard (CA)

(73) Assignee: NATIONAL RESEARCH COUNCIL OF CANADA, Ottawa, ON (CA)

( * ) Notice: Subject to any disclaimer, the term of this patent is extended or adjusted under 35 U.S.C. 154(b) by 290 days.

(21) Appl. No.: 14/240,168

(22) PCT Filed: Aug. 24, 2011

(86) PCT No.: PCT/CA2011/000955
§ 371 (c)(1),
(2), (4) Date: Feb. 21, 2014

(87) PCT Pub. No.: WO2013/026125
PCT Pub. Date: Feb. 28, 2013

(65) Prior Publication Data
US 2014/0184022 A1   Jul. 3, 2014

(51) Int. Cl.
*B06B 1/06* (2006.01)
*H01L 41/047* (2006.01)
*G01N 29/34* (2006.01)
*H01L 41/187* (2006.01)
*H01L 41/318* (2013.01)
(Continued)

(52) U.S. Cl.
CPC ............. *H01L 41/0477* (2013.01); *B06B 1/06* (2013.01); *B06B 1/0688* (2013.01); *G01N 29/34* (2013.01); *H01L 41/0805* (2013.01); *H01L 41/187* (2013.01); *H01L 41/318* (2013.01); *H01L 41/331* (2013.01); *H01L 41/1876* (2013.01); *Y10T 29/42* (2015.01)

(58) Field of Classification Search
CPC ........ B06B 1/06; B06B 1/0603; B06B 1/0688; H01L 41/187
USPC ......................................... 310/322, 334, 335
See application file for complete search history.

(56) References Cited

U.S. PATENT DOCUMENTS

| | | |
|---|---|---|
| 2,430,013 A | 11/1947 | Hansell |
| 3,376,438 A | 4/1968 | Colbert |
| 3,989,965 A | 11/1976 | Smith et al. |

(Continued)

FOREIGN PATENT DOCUMENTS

| | | |
|---|---|---|
| CN | 101219897 | 7/2008 |
| WO | WO0045826 | 8/2000 |

OTHER PUBLICATIONS

Bardaine A. et al., Improvement of composite sol-gel process for manufacturing 40 um piezoelectric thick films, Journal of the European Ceramic Society 28, 2008, pp. 1649-1655.

(Continued)

*Primary Examiner* — Derek Rosenau
(74) *Attorney, Agent, or Firm* — Catherine Lemay

(57) ABSTRACT

A piezoelectric film having a porosity between 20 and 40%, a thickness ranging from tens of microns to less than a few millimeters can be used to form an ultrasonic transducer UT for operation in elevated temperature ranges, that emit pulses having a high bandwidth. Such piezoelectric films exhibit greater flexibility allowing for conformation of the UT to a surface, and obviate the need for couplings or backings. Furthermore, a method of fabricating an UT having these advantages as well as better bonding between the piezoelectric film and electrodes involves controlling porosity within the piezoelectric film.

10 Claims, 2 Drawing Sheets

(51) Int. Cl.
  *H01L 41/08* (2006.01)
  *H01L 41/331* (2013.01)

(56) References Cited

U.S. PATENT DOCUMENTS

| | | | |
|---|---|---|---|
| 4,016,530 | A | 4/1977 | Goll |
| 4,751,013 | A | 6/1988 | Kaarmann et al. |
| 5,224,972 | A | 7/1993 | Frye et al. |
| 5,585,136 | A | 12/1996 | Barrow et al. |
| 5,958,815 | A | 9/1999 | Loebmann et al. |
| 6,066,581 | A | 5/2000 | Chivukula et al. |
| 6,111,339 | A | 8/2000 | Ohya et al. |
| 6,432,238 | B1 | 8/2002 | Yun et al. |
| 6,761,692 | B2 | 7/2004 | Angelsen et al. |
| 6,897,601 | B2 * | 5/2005 | Birth .................. H01L 41/053 310/326 |
| 7,544,244 | B2 | 6/2009 | Sakashita et al. |
| 7,807,216 | B2 | 10/2010 | Zhu et al. |
| 2008/0139946 | A1 | 6/2008 | Adachi et al. |
| 2008/0182128 | A1 | 7/2008 | Boy et al. |
| 2010/0119800 | A1 | 5/2010 | Yokoyama et al. |

OTHER PUBLICATIONS

Chen, Ding and Xiao, Ting, One-step synthesis of Zn to single-phase nanocrystalline ZnO by solid-liquid reaction ball milling assisted by ultrasonic wave, J. Am. Ceram. Soc., 93, 2010 pp. 2675-2678.

Inoue, T. et al., Design of ultrasonic transducers with multiple acoustic matching layers for medical application, IEEE Transactions on Ultrasonics, Ferroelectrics, and Frequency Control, vol. UFFC-34, No. 1, 1987, pp. 8-16.

Kobayashi M. et al, Flexible Ultrasonic Transducers, IEEE Transactions on Ultrasonics, Ferroelectrics, and Frequency Control, vol. 53, No. 8 2006 pp. 1478-1486.

Kobayashi M. et al., High-temperature piezoelectric film ultrasonic transducers by a sol-gel spray technique and their application to process monitoring of polymer injection molding, IEEE Sensors Journal, vol. 6, No. 1, 2006, pp. 55-62.

Kossoff, George, The effects of backing and matching on the performance of piezoelectric ceramic transducers, IEEE Transactions on Sonics and Ultrasounds, vol. SU-13, No. 1, 1966, pp. 20-30.

Pierre, A.C., Porous sol-gel ceramics, Ceramics International 23, 1997, pp. 229-238.

Thurston, R.N. et al., Reference for Modern Instrumentation, Techniques, and Technology, Ultrasonic Instruments and Devices I, vol. 23, Academic Press, p. 52, 1999.

International Preliminary Report on Patentability of corresponding PCT Application No. PCT/CA2011/000955 mailed on Feb. 25, 2014.

International Search Report and Written Opinion of corresponding PCT Application No. PCT/CA20111000955 mailed on Mar. 20, 2012.

English Abstract of CN101219897.

* cited by examiner

POROSITY CONTROL IN PIEZOELECTRIC FILMS

CROSS-REFERENCE RELATED APPLICATIONS

This application is a national phase entry of International Patent Application No. PCT/CA2011/000955 filed Aug. 24, 2011 the entire content of which is herein incorporated by reference.

FIELD OF THE INVENTION

The present invention relates in general to a technique for forming a piezoelectric film with controlled porosity, especially for the fabrication of ultrasonic transducers as may be utilized for nondestructive testing (NDT), structural health monitoring (SHM), or biomedical diagnostics.

BACKGROUND OF THE INVENTION

There is substantial demand for piezoelectric ultrasonic transducers (UTs), such as those formed by piezoelectric films, sandwiched between two electrode layers. In a wide variety of contexts, the ability to propagate ultrasonic waves in a medium, and/or detect waves thus propagated, is highly useful, for example, in ultrasonic non-destructive testing (NDT) and structural health monitoring (SHM) of materials, components or structures. In some applications, there is a particular need: to use broad frequency bandwidth UTs; to perform ultrasonic generation or detection at elevated temperatures; or to conform the piezoelectric transducer to components or structures that have complex shapes, such as curved surfaces like pipes. For example, there is a need to monitor the thickness of pipes in a power plant that is subjected to high temperatures, wear, corrosion or erosion. If a high accuracy of the thickness measure is desired, a broad bandwidth UT is advantageous. Typically it is highly desirable that UTs operate in the broadband frequency regime in which their 6 dB bandwidth exceeds 30%, to emit/detect ultrasonic pulses that have only a few ring-down cycles, allowing for high precision thickness measurement and also the defect location, if any. Therefore there are high demands for UTs that can perform ultrasonic measurements efficiently and accurately (a) on curved surfaces, (b) at high temperatures with capability to sustain thermal cycles from low temperature such as −80° C. to elevated temperatures such as 200° C., 500° C., 800° C. or 1000° C.; and (c) a broad frequency bandwidth. It is also desirable to have flexible UTs which have the above (a), (b) and (c) features.

While broad frequency bandwidth can be provided by mechanically damping the UT, e.g. with a backing between a top electrode of the UT and its air interface (i.e. on the opposite side of the inspected surface). Backings attenuate the ultrasonic (mechanical) energy, as is known in the art (see, for example U.S. Pat. No. 3,376,438 to Colbert [1], U.S. Pat. No. 3,989,965 to Smith et al. [2], and G. Kossoff, "The effects of backing and matching on the performance of piezoelectric ceramic transducers", IEEE Trans. on Sonics and Ultrasonics, vol. SU-13, pp. 20-30, March 1966. [3]). When the piezoelectric element is excited by the electrical signal, the generated ultrasonic wave transmitted into the backing material will be attenuated by the mechanisms of absorption and/or scattering. It suppresses multiple reflected echoes inside the piezoelectric element and thus it will have the broadband frequency characteristics. However, the use of backings) in accordance with the prior art, introduce other problems. Backing materials often use epoxies as the host materials in which metal or ceramic powders are filled in order to increase the acoustic impedance of the backing and match with that of the UTs. This backing makes the previous arts bulky, heavy, and not flexible and difficult to be used to evaluate materials, components and structures with complex surfaces. In addition, epoxies cannot sustain a temperature more than several hundred degrees Celsius so that it is not suitable for high temperature applications. It should also be noted that for measurements at high temperatures, thermal cycles may happen. Because of the large difference in thermal expansion coefficients and thermal conductivity between the epoxy and the thin metallic electrode of the UT, epoxy-based backings tend to detach from the) electrode after several thermal cycles. Such detachment causes an abrupt failure that degrades the broadband frequency characteristics of the UTs.

Another approach to achieving broad frequency bandwidth UTs is to insert a matching layer between the UT and inspected surface, the matching layer having the proper acoustic impedance according to those of the piezoelectric transducer material and the medium, as known in the art (see, for example [3], U.S. Pat. No. 2,430,013 to Hansell [4], or U.S. Pat. No. 4,016,530 to Goll [5]). When one layer with quarter wavelength thickness and proper acoustic impedance, i.e. square root of the product of the acoustic impedance of piezoelectric material and that of the target to be monitored, are inserted between the UT and the medium, the bandwidth can be increased.) However, it is relatively difficult to obtain such a proper acoustic impedance material. Also, the increase of bandwidth using this technique is limited. Multiple layers could be used to accomplish the acoustic impedance conditions, although it can cause further loss and the design becomes more complicated. Furthermore, acoustic impedance will change when the temperature changes, and each material has a different acoustic impedance dependence with temperature. Therefore, it is at least difficult to provide high quality impedance matching with a variety of ultrasonic media, for operation across a wide temperature range, which is often required for NDT and SHM applications.

According to the teachings of U.S. Pat. No. 4,751,013 to Kaarmann et al. [6], porosity is introduced into piezoelectric films with a view to reducing shear wave excitation at the transducer edge and to match the acoustic impedance of the UT to that of the substrate to be inspected, so that more ultrasonic energy can be transmitted from D the UT to the substrate. There is no information relating porosity to frequency bandwidth, or temperature of operation, and no evidence that bonding during thermal cycle or flexibility would be provided. Furthermore, the disclosed method of fabricating porous piezoelectric films was by mixing piezoelectric powder, binder, and polymer in the form of small particles which were fired out during calcination process. Since the sizes of pearl polymers were between 10 μm to 40 μm which are large, high ultrasonic attenuation and strong scattering at high ultrasonic operation frequency are expected.

U.S. Pat. No. 6,111,339 to Ohya et al. [7] teaches manufacture of porous piezoelectric sheets. There is no information relating the porosity to the frequency bandwidth, or operating temperature, and no evidence that bonding during thermal cycle or flexibility would be provided. Furthermore, the disclosed method of fabricating porous piezoelectric films was by mixing piezoelectric powder, binder, and combustible powder such as poly methyl methacrylate which will burn out during heating process. The pore sizes in this method were between 5 and 25 μm which are still large and result in high ultrasonic attenuation due to strong scattering at high ultrasonic operation frequency.

U.S. Pat. No. 5,585,136 to Sekimori et al. [8] teaches a particular fabrication technology, sol-gel technique, to produce piezoelectric films for ultrasonic transducers. The invention reported is related to how to reduce the porosity in order to fabricate dense piezoelectric films. There is no information relating the porosity to the frequency bandwidth, or temperature of operation, and no evidence that bonding during thermal cycle or flexibility would be provided. Also US patent application US2008/182128 to Boy et al. [9] teaches a method to produce low porosity piezoelectric films with high piezoelectric constant by multiple impregnation of the porous film with sol-gel piezoelectric precursor solution. This method is laborious and results in piezoelectric transducers that are narrow band and do not have the high temperature capabilities.

It is also known to provide high porosity UTs. For example, U.S. Pat. No. 5,958,815 to Loebmann et al. teaches a method of producing a particular piezoelectric film for a transducer designed for coupling to a gaseous medium. As noted in the field of that invention, the notably different acoustic impedance of solids and gasses make conventional ultrasonic sensors and actuators made of dense ceramic and ceramic-polymer composites, of limited use in coupling to gaseous media. Loebmann therefore) only advocates use of porous UTs for coupling to coupling with gaseous media. The prior art shows a bias for dense UTs when coupling with solids or liquids. It will be noted that their UTs are about 80% porous, making them ill suited for coupling to solid or liquid media.

Accordingly there is a need for broad frequency bandwidth ultrasonic transducers capable of operating at high temperatures such as 200° C., 500° C., 800° C. or 1000° C., preferably without requiring a backing.

SUMMARY OF THE INVENTION

Applicant has discovered, unexpectedly, that porosity, to a controlled degree, is an important feature for designing UTs for operation in specific temperature ranges, and for emitting pulses having high bandwidth. Furthermore, higher porosity piezoelectric films exhibit greater flexibility allowing for conformation of the UT to a surface. The UTs may be mounted without any coupling or backing, which is advantageous in many applications, may be provided for operation at elevated temperatures, or within a particular range of elevated temperatures, and may exhibit better bonding between the piezoelectric film and electrodes than non-porous, or otherwise fabricated piezoelectric films.

In accordance with the present invention an ultrasonic transducer (UT) is provided. The UT comprising a piezoelectric film sandwiched between two electrodes, wherein the film is 2 microns to 2 mm thick, has a porosity of 15-40% with micron-scale or sub-micronscale pores, and is principally composed of piezoelectric powders having micron or submicron sizes mixed with a residue of a binder. The thickness may be 10 microns to 1 mm, or 50 microns to 1 mm. The porosity may be 22-40%, 25-40%, 30-38%, 30-35%, or 22-32%. The binder residue may include 1 residue of a liquid or gel oxidizing agent that formed an intermediate oxidation layer on at least one of the electrodes, 2 a residue deposited after thermal treatment that is piezoelectric or 3 a residue deposited after thermal treatment that is chemically and thermally stable at a desired operating temperature of the UT, that has a high dielectric constant, preferably higher than the powders. The binder residue may include two or more of these 3, and may include substantially nothing other than these 3. The film may consist of the binder residue and powders.

The electrode may be a high electrical conductivity material with minimal and non-fragile oxidation at temperatures throughout a desired operating temperature of the UT.

The UT may have a −6 dB bandwidth greater than 30%, 60%, 70%, or 100%, such as a range of 70-200%, 100-150%, or 93-133%.

One of the electrodes may be directly coupled to a surface of a part of an apparatus for emitting or detecting ultrasonic waves in the part, without an impedance matching layer, or a backing. The UT may be designed for high-temperature applications.

Also, in accordance with the present invention a method of producing an ultrasonic transducer (UT) with controlled porosity is provided. The method comprises providing a bottom electrode for the UT; mixing a binder and piezoelectric powders to form a slurry; depositing the slurry, and drying, sintering the deposited slurry to build up a piezoelectric film on the bottom electrode; poling the piezoelectric film to make it piezoelectricly active; applying a top electrode for the UT; and providing an electric circuit for controlling the piezoelectric film. A size distribution, shape distribution and porosity of the powders, and an abundance of the binder relative to that of the piezoelectric powders in the slurry as deposited, are controlled to provide a desired porosity for the piezoelectric film that is between 15-40%, 20-40%, 25-40%, 30-38%, 30-35%, or 22-32%.

The bottom electrode may be a high electrical conductivity material with minimal and non-fragile oxidation at temperatures throughout a desired operating temperature of the UT, and may be bonded to a surface of a part to be tested ultrasonically. The binder may be selected to leave the residue described above.

In accordance with the method, the powders may constitute about 40% to about 90% molar ratio of the mixture, with the balance being a binder (ignoring the entrained air). The binder is preferably a ceramic precursor, such as a liquid or sol-gel. For example, the mixture may include a molar ratio of around 80:20-40:60 powder to precursor, 80:20-60:40, or 75:25-70:30. Mixing may involve limited comminuting of the powders, to provide sufficient porosity to the film, for example by limiting the amount, duration or degree of ball milling, or by ultrasonic excitation of the slurry to provide sufficient mixing, without substantial comminution. The slurry may be deposited by screen printing, stencil printing, spray coating, tape casting, dip coating or spin coating the slurry onto the electrode, and may preferably be applied by spray coating, as with controlled spray velocity distribution and distance. A number of coats may be applied to provide a layer thickness prior to drying, sintering and poling, the layer thickness controlled to provide sufficient drying to impart a desired porosity to the resulting film.

Further features of the invention will be described or will become apparent in the course of the following detailed description.

BRIEF DESCRIPTION OF THE DRAWINGS

In order that the invention may be more clearly understood, embodiments thereof will now be described in detail by way of example, with reference to the accompanying drawings, in which.

DESCRIPTION OF PREFERRED EMBODIMENTS

Figure 1:
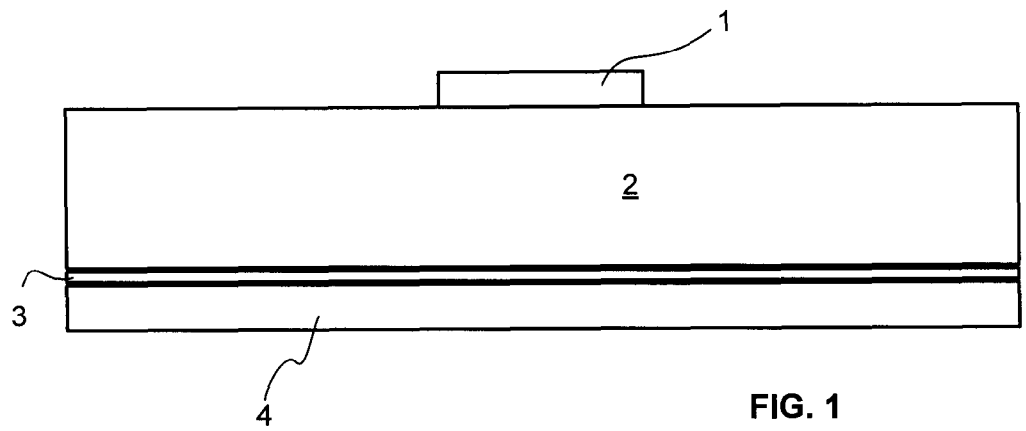
FIG. 1 is a schematic illustration of a thin substrate UT in accordance with an embodiment of the invention.

The present invention provides piezoelectric films having improved high temperature operation, and bandwidth, provided by porosity control, and teaches how to fabricate such piezoelectric films. The preferred applications of the invented piezoelectric films are for ultrasonic transducers (UT) for NDT, SHM, and biomedical diagnostics. The thickness of such piezoelectric films may range from several microns to less than two millimeters. The porosity of the piezoelectric film may be controlled between about 15% and about 40%. The UTs may be designed to operate in a broad ultrasonic bandwidth, at temperature of up to 1000° C., or may be flexible when such piezoelectric films are directly coated onto thin membranes made of metals or polymer composites. Herein a broad ultrasonic bandwidth refers to a −6 dB bandwidth of more than 30% of the center operation frequency. Such flexible UTs can conform to curved surfaces such as pipes.

Thick porous piezoelectric film UTs consisting of a top electrode, a porous piezoelectric film and a bottom electrode, on substrate are preferred. The porous piezoelectric films are typically made of ceramics such lead-zirconate-titanate (PZT), bismuth titanate, lithium niobate (LiNbO$_3$), etc. The average size of the pores is of microns or submicrons.

To fabricate the UT, a bottom electrode is deposited onto a substrate. Where desired, the substrate may be flexible. The bottom electrode may be composed of metals or alloys suitable for high temperature operation, having high electrical conductivity, with minimal and non-fragile oxidation at the desired operating temperatures. For temperatures up to 850° C., electrodes such as nickel, platinum, titanium, stainless steel, silver, etc. may be used. Both metals and polymer composites are preferred, provided they can resist temperatures of the heat treatment (typically above 300° C.), and the desired operating temperature range. Fabrication temperature could be lowered down to 150° C. with signal strength and chemical stability sacrifice. The metal substrates can be nickel, platinum, titanium, stainless steel, silver, etc., while polymer composites can be glass fiber composites, carbon fiber composites, polyimide based composites, etc. The bottom electrode can be formed on the thin substrate by electroplating or electroless plating, spray coating, painting, vacuum deposition, etc. The bottom electrode can alternatively be the substrate.

A mixture is prepared with piezoelectric film materials in powder form, having micron or submicron sizes, with oxidizing binders in a liquid or gel form. The composition of the piezoelectric powders is preferably chosen for high piezoelectricity at the desired operating temperature, which may be at a high operating temperature. The mixture may be deposited onto the bottom electrode, by screen printing, stencil printing, spray coating, tape casting, dip coating, and spin coating, for example, to produce a layer of the mixture.

The layer is heat treated, during which treatment the materials are dried and calcined, some portions of the binder evaporate and react with the materials, resulting in a porous piezoelectric film. The deposition of layers and drying may alternate, or may be in series, depending on the duration and desired degree of the drying. The binder residue, after the heat treatment, preferably has a high dielectric constant, preferably higher than that of the piezoelectric powders. Such high dielectric constant is crucial for the electrical poling of the porous piezoelectric film together with the bottom electrode. After the calcining, the film is subjected to a high DC voltage, which provides electrical energy to pole the material, aligning dipoles of the piezoelectric materials, making the material piezoelectricly active. During the electrical poling, an electric field extends across both the piezoelectric powders and the binder material, and so it is important that the binder residue does not conduct electricity, as this would interfere with the poling.

Preferably the binders create an oxidation layer with the bottom electrode during the heat treatment, resulting in strong adhesion between the porous film and bottom electrode. In order to strengthen the piezoelectricity of the film, the binder material after the heat treatment and electrical poling, is preferred to be a piezoelectric material that can work at the desired temperatures, such as up to 200° C., 500° C., 800° C. or 1000° C. Suitable binders include piezoelectric ceramic precursors of a wide variety of recipes known in the art, each having different limitations and advantages. Some examples are provided in the following papers, the contents of which are incorporated herein by reference: PZT sol-gel precursors such as D. Barrow, C. V. R. V. Kumar, R. Pascual and M. Sayer, "Crystallization of sol gel PZT on aluminum and platinum metallizations", Mat. Res. Soc. Symp. Proc., vol. 243, pp. 113-122, 1981, N. Tohge, S. Takahashi and T. Minami, "Preparation of PbZrO$_3$—PbTiO$_3$ ferroelectric films by the sol-gel process", J. Am. Ceram. Soc., vol. 74, no. 1, pp. 67-71, 1991, and T. Olding, B. Leclerc, M. Sayer, "Processing of multilayer PZT coatings for device purposes", Integrated Ferroelectrics, vol. 26, pp. 225-241, 1999; and bismuth titanate sol-gel precursors such as X. S. Wang, Y. J. Zhang, L. Y. Zhang, X. Yao, "Structural and dielectric properties of Bi$_4$Ti$_3$O$_{12}$ thin films prepared by metalorganic solution deposition", Appl. Phys. A, vol. 68, pp. 547-552, 1999, P. Fuierer and B. Li, "Nonepitaxial orientation in sol-gel bismuth titanate films", J. Am. Ceram. Sic., 85 [2], pp. 299-304, 2002, and M. Toyoda, Y. Hamaji, K. Tomono, and D. A. Payne, "Synthesis and characterization of Bi$_4$Ti$_3$O$_{12}$ thin films by sol-gel processing", Jpn. J. Appl. Phys., vol. 32, pp. 4158-4162, September 1993.

The top electrode layer is then deposited. The top electrode layer may have similar requirements, but may not need to suffer exposure to the heat treatment step, as it may be deposited after heat treatment. Alternatively the top electrode may be deposited prior to heat treatment and poling, whereby the same oxidation layer is created between the piezoelectric film and both electrodes.

The porosity is necessary to achieve the broad bandwidth, the high operation temperature and flexibility of the UTs. The control of the porosity and the average sizes of the pores can be achieved by adjusting the sizes of the piezoelectric powders, the mixing ratios of the piezoelectric powders with respect to binders, compositions of the binders, deposition (such as spray coating parameters: coating velocity and thickness), and heat treatment parameters. Principally, the size of the powders, and mixing conditions of the precursor, thickness of the layer of mixture, and the weight ratio of powder to precursor, have been found to reliably control the porosity of the resulting film in some applications. It is conventional to ball mill the mixture prior to spraying, as this has the effect of comminuting the powders, densifying the mixture, and making the mixture more homogeneous. By ultrasonic mixing instead of ball milling, the powder is not comminuted, leaving larger pores. These larger pores are filled with the precursor solution. By limiting the amount of precursor solution, therefore, it is possible to further increase porosity of the film.

Applicant has observed that in general, the lower the porosity, the narrower the UT's frequency bandwidth (ceteris paribus). A piezoelectric porous film having porosity less than about 10% typically needs to have a backing to achieve broad bandwidth emission/detection. Backing materials are taught in the prior art references [1-3]. A piezoelectric porous film having porosity higher than 40% will typically have insufficient piezoelectricity for coupling to solid or liquid media, and will typically exhibit high ultrasonic scattering losses at higher ultrasonic frequencies.

Applicant has experimented with a variety of techniques for forming a lead-zirconate-titanate (PZT), and bismuth-titanate powder-based UTs. Specifically the techniques used are similar to those taught in the papers listed above, and involve producing a precursor solution, and adding a powder to the mixture, spraying the mixture, calcining (sintering) and poling, and applying electrodes. The specific precursor is not believed to be essential to the result, but how to best achieve the desired porosity can vary somewhat between formulations. There are numerous recipes for precursors, and different recipes produce UTs having different power, thickness, efficiency, durability, operating temperature, and cost. In general the first parameters to consider for producing a desired bandwidth, flexibility and thermal operation (including thermal cycling resistance), are powder size, shape, porosity and distribution, as well as the ratio of the powders to precursor in the mixture, and thickness of the layer. Other factors such as deposition (spray) parameters, age of the precursor, thermal treatment parameters, and nature of the powder and precursor all come into play, and may be varied. It is within the scope of the person of ordinary skill to adapt known fabrication processes to produce the desired porosity of the UTs.

For example, a series of UTs were produced with the PZT piezoelectric material. The specific precursor is a sol gel containing titanium butoxide, zirconium butoxide, and lead acetate trihydrate. With the precursor solution thus synthesized, PZT powder (200 mesh size) and the precursor were mixed. As is conventional, multiple layers were applied onto a metal substrate by spray coating. Before thermal treatment, 4 or 8 coats were sprayed (by hand) to obtain a coating having homogeneous thickness. Films were created with each of five layers dried and fired at 120° C. and 650° C. for 5 minutes each. The film was poled with corona discharge at 120° C. A 25 kV potential difference was used to generate the corona discharge. After the poling, polishing was executed in order to have uniform thickness. Silver top electrodes were painted onto thin porous PZT films at room temperature.

According to the first UT, the mixing of the PZT powder (40 wt. %) and precursor (60 wt. %) was performed in a ball mill. The ball milling was performed for 2 days, i.e. long enough for saturation of size reduction, using balls of Burundum (0.5" OD, 0.5" height). It is estimated that the ball milling reduced the powder size from about 10-20 μm (median ~12 μm) prior to milling, to about 0.5-2 μm after milling. According to the second UT, the powder to precursor ratio was 33:67 wt. % to allow for more precursor to occupy the greater voids between the larger particles, as the powders were mixed in an ultrasonic bath and not ball milled. Except for a first layer, which had 4 coats, 8 coats were applied per layer prior to thermal treatment, but otherwise the method was the same. According to the third UT, the powder to precursor ratio that of the first UT, and the mixing and layering were applied as per the second UT.

The porosity of the piezoelectric film in the first UT was determined to be 22% by SEM observation. As a UT, it showed signal strength, that is comparable to commercial ultrasonic transducers. The bandwidth was calculated from the centre frequency and upper/lower −6 dB frequencies, and value obtained was 94%. The calculated velocity, derived from the first peak frequency and the film thickness, was 977 m/s. The second UT had a film porosity of 27% by SEM observation, showed a signal strength 16 dB lower than that of the first UT, with a −6 dB bandwidth of 122%, and a velocity of 888 m/s. The third UT had a film porosity of 32%, a signal strength 26 dB lower than that of the first UT, a −6 dB bandwidth of 130%, and a 648 m/s ultrasonic velocity. Given the porosities, the UTs will have better flexibility, higher thermal operating ranges, better resistance to thermal cycling than dense UTs that are usually preferred because of their higher signal strengths.

The porosity of the piezoelectric film enables the UT to exhibit three advantages: (a) broad frequency bandwidth emission/detection, (b) high operating temperature and resistance to thermal cycling, and (c) flexibility. The porosity of the piezoelectric film, which is coated directly onto the bottom electrode with high electrical conductivity, allows a large thermal expansion coefficient difference between the piezoelectric porous ceramic film and the bottom electrode, without increased risk of delamination. It also means that such porosity enables the porous piezoelectric transducers to operate at high temperatures including thermal cycle conditions. Flexibility of the UTs may also be desired. The flexibility of a dense piezoelectric thick film (i.e. 0% porosity and thickness >10 μm) is poor. The porosity of the thick piezoelectric porous film together with the thinness of the top electrode, bottom electrode, and thin substrate enable that the porous UT can be adapted to curved surfaces such as pipes.

FIG. 1 is a schematic illustration of a UT in accordance with an embodiment of the present invention. It will be appreciated that protective layers and other coatings may be added to this structure, as well as circuitry for regulating current between the top and bottom electrodes. The embodiment shown is of a UT, consisting of a top electrode 1, a porous piezoelectric film 2, and a bottom electrode 3 on a thin substrate 4. The total thickness of the porous piezoelectric film is less than two millimeters. The porous piezoelectric film is formed from piezoelectric ceramic powders having an average size in the micron or submicron range, and the size may be visible from electron microscope imaging after the heat treatment. The thin substrate 4 can be composed of one or more metals, or polymer composites. The thickness should be low enough to ensure the flexibility of the UT. The UT, as shown in FIG. 1, can be conformed to a pipe.

Figure 2:
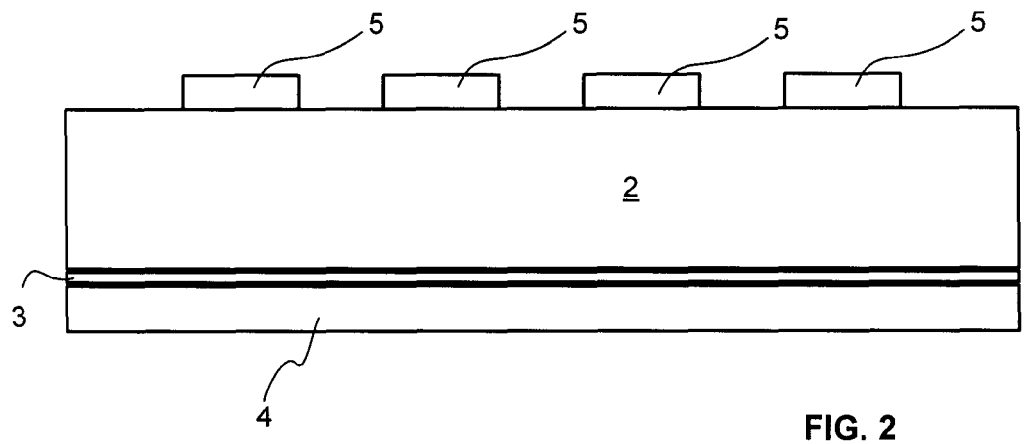
FIG. 2 is a schematic illustration of a thin substrate UT array in accordance with an embodiment of the invention.

Another embodiment of the invention is shown in FIG. 2, in which multiple top electrodes 5 of the porous UT are provided, to form a UT array. The array can be in the form of circular or square dots, parallel straight lines, partial and full cylindrical and circular lines with separation distances between the adjacent dots or lines, for example. Each top electrode represents the active area of one UT. The array can be operated as multiple individual UTs or a phase array which can provide electronic scanning and focusing capability. Otherwise, this embodiment is similar to that shown in FIG. 1.

Figure 3:
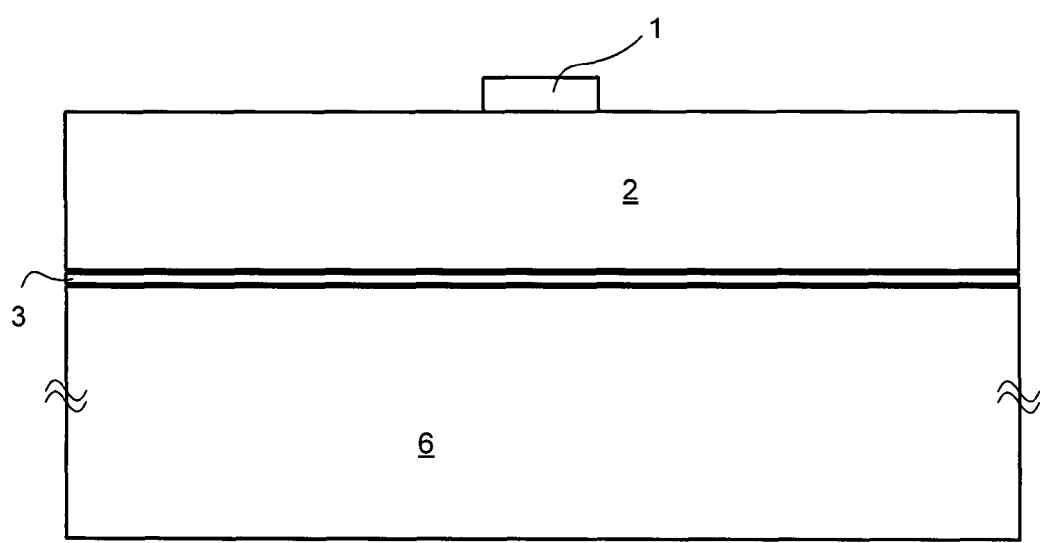
FIG. 3 is a schematic illustration of a thick substrate UT in accordance with an embodiment of the invention.

Another embodiment of the invention is shown in FIG. 3, in which porous UTs are directly deposited on the thick substrate 6. As will be understood by those of skill in the art, a layer is thick if it has a thickness of more than one ultrasonic wavelength. The thick substrate 6 can be composed of metals or polymer composites with complex shapes such as pipes.

Figure 4:
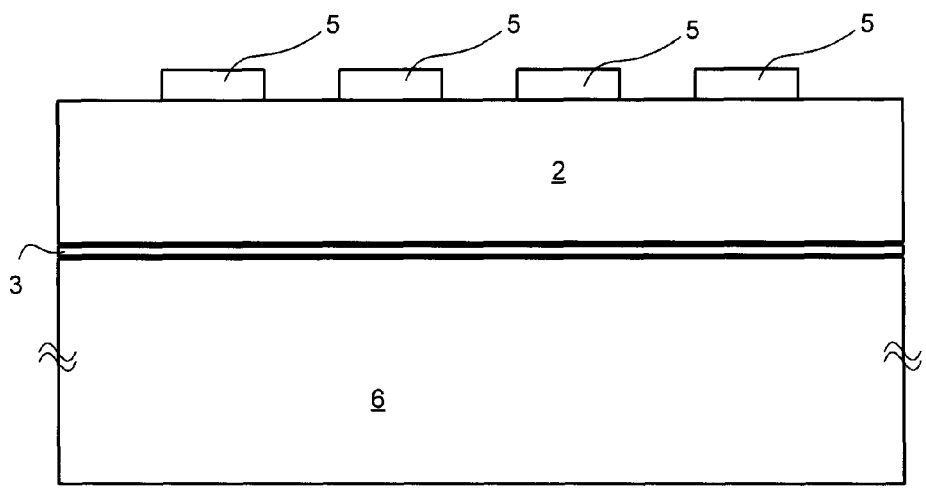
FIG. 4 is a schematic illustration of a thick substrate UT array in accordance with an embodiment of the invention.
Figure 5:
FIG. 5 is a microscope image of a top surface of a piezoelectric film in accordance with an example of the invention.
Figure 6:
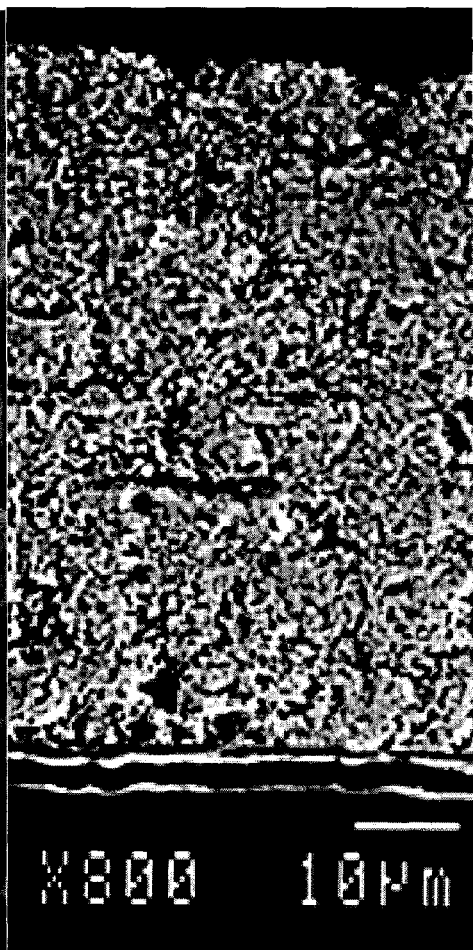
FIG. 6 is a microscope image of a cross-section of a piezoelectric film in accordance with an example of the invention.

Another embodiment of the invention is shown in FIG. 4, in which multiple top electrodes 5 of the porous UTs can be in array configurations on a substrate 6 that is more than one ultrasonic wavelength thick. In the drawings, like reference numerals refer to like features, and the descriptions of the features are not repeated for each drawing.

Other advantages that are inherent to the structure are obvious to one skilled in the art. The embodiments are described herein illustratively and are not meant to limit the scope of the invention as claimed. Variations of the foregoing embodiments will be evident to a person of ordinary skill and are intended by the inventor to be encompassed by the following claims.

The invention claimed is:

1. An ultrasonic transducer (UT) comprising a piezoelectric film sandwiched between two electrodes, wherein the film:
   is 2 microns to 2 mm thick;
   has a controlled porosity of 15-40% with micron-scale or sub-micron scale pores; and
   comprises piezoelectric powders having micron or sub-micron sizes mixed with a residue of a binder, wherein the binder residue comprises residue of a liquid or gel oxidizing agent that forms an intermediate oxidation layer on at least one of the electrodes, said at least one electrode formed of an electrically conductive material so that the UT is endowed with an ultrasonic bandwidth of at least 30%.

2. The UT of claim 1 wherein the binder residue is:
   a residue deposited after thermal treatment that is piezoelectric; or
   a residue deposited after thermal treatment that is chemically and thermally stable at a desired operating temperature of the UT, and having a high dielectric constant.

3. The UT of claim 1 wherein the binder residue is:
   a residue deposited after thermal treatment that is piezoelectric; and
   a residue deposited after thermal treatment that is chemically and thermally stable at a desired operating temperature of the UT, and having a high dielectric constant.

4. The UT of claim 1 wherein the film consists of the powders and the binder residue.

5. The UT of claim 1 wherein the −6 dB bandwidth of the UT is greater than 30%.

6. A combination comprising:
   a part of an apparatus, the part having a first surface and a second surface opposite the first surface; and
   a high-temperature ultrasonic transducer (UT) comprising a piezoelectric film sandwiched between two electrodes, and control circuitry for the film, wherein the film:
      is 2 microns to 2 mm thick;
      has a controlled porosity of 15-40% with micron-scale or sub-micron scale pores; and
      comprises piezoelectric powders having micron or sub-micron sizes mixed with a residue of a binder, wherein the binder residue comprises residue of a liquid or gel oxidizing agent that forms an intermediate oxidation layer on at least one of the electrodes, said at least one of the electrodes being formed of an electrically conductive material; and
   wherein one of the electrodes is directly coupled to the first surface for emitting or detecting ultrasonic waves in the part at the second surface, opposite the film, without an impedance matching layer, and the UT does not include a backing.

7. The high-temperature UT of claim 6 wherein the binder residue is:
   a residue deposited after thermal treatment that is piezoelectric; or
   a residue deposited after thermal treatment that is chemically and thermally stable at a desired operating temperature of the UT, and having a high dielectric constant, preferably higher than that of the powders.

8. The high-temperature UT of claim 6 wherein the binder residue is:
   a residue deposited after thermal treatment that is piezoelectric; and
   a residue deposited after thermal treatment that is chemically and thermally stable at a desired operating temperature of the UT, and having a high dielectric constant, preferably higher than that of the powders.

9. The high-temperature UT of claim 6 wherein the film consists of the powders and the binder residue.

10. The high-temperature UT of claim 6 wherein the −6 dB bandwidth of the UT is greater than 30%.

* * * * *

UNITED STATES PATENT AND TRADEMARK OFFICE
CERTIFICATE OF CORRECTION

PATENT NO. : 9,548,439 B2
APPLICATION NO. : 14/240168
DATED : January 17, 2017
INVENTOR(S) : Makiko Kobayashi et al.

It is certified that error appears in the above-identified patent and that said Letters Patent is hereby corrected as shown below:

In the Claims

Column 10, Lines 31 – 50, replace Claims 7-10 as follows:

7. The combination of claim 6 wherein the binder residue is:
    a residue deposited after thermal treatment that is piezoelectric; or
    a residue deposited after thermal treatment that is chemically and thermally stable
at a desired operating temperature of the UT, and having a high dielectric constant,
preferably higher than that of the powders.

8. The combination of claim 6 wherein the binder residue is:
    a residue deposited after thermal treatment that is piezoelectric; and
    a residue deposited after thermal treatment that is chemically and thermally stable
at a desired operating temperature of the UT, and having a high dielectric constant,
preferably higher than that of the powders.

9. The combination of claim 6 wherein the film consists of the powders and the binder residue.

10. The combination of claim 6 wherein the -6 dB bandwidth of the UT is greater than 30%.

Signed and Sealed this
Sixth Day of March, 2018

Andrei Iancu
*Director of the United States Patent and Trademark Office*